US006312391B1

(12) United States Patent
Ramadhyani et al.

(10) Patent No.: US 6,312,391 B1
(45) Date of Patent: Nov. 6, 2001

(54) THERMODYNAMIC MODELING OF TISSUE TREATMENT PROCEDURE

(75) Inventors: Satish Ramadhyani, Minneapolis; Jonathan L. Flachman, Robbinsdale; Eric N. Rudie, Maple Grove, all of MN (US)

(73) Assignee: Urologix, Inc., Minneapolis, MN (US)

( * ) Notice: Subject to any disclaimer, the term of this patent is extended or adjusted under 35 U.S.C. 154(b) by 0 days.

(21) Appl. No.: 09/505,587

(22) Filed: Feb. 16, 2000

(51) Int. Cl.$^7$ ........................................ A61B 5/00
(52) U.S. Cl. ............................................... 600/549
(58) Field of Search .............................. 600/549, 300; 607/102, 101, 97, 105

(56) References Cited

U.S. PATENT DOCUMENTS

| | | | |
|---|---|---|---|
| Re. 34,938 | 5/1995 | Serikov et al. | 128/691 |
| 4,852,027 | 7/1989 | Bowman et al. | 364/557 |
| 4,859,078 | 8/1989 | Bowman et al. | 374/44 |
| 5,220,927 | * 6/1993 | Astrahan et al. | 600/549 |
| 5,304,214 | * 4/1994 | DeFord et al. | 607/105 |
| 5,413,588 | * 5/1995 | Rudie et al. | 607/101 |
| 5,620,479 | * 4/1997 | Diederich | 607/97 |
| 5,620,480 | * 4/1997 | Rudie | 607/101 |
| 5,841,288 | 11/1998 | Meaney et al. | 324/639 |
| 5,919,135 | 7/1999 | Lemelson | 600/407 |
| 5,978,691 | 11/1999 | Mills | 600/334 |
| 6,122,551 | * 9/2000 | Rudie et al. | 607/102 |

OTHER PUBLICATIONS

"Detailed Interstitial Temperature Mapping During Treatment With A Novel Transurethral Microwave Thermoablation System In Patients With Benign Prostatic Hyperplasia" by Larson et al., *The Journal of Urology*, vol. 159, pp. 258–264, Jan. 1998.

"Transurethral Thermal Therapy (T3) For The Treatment Of Benign Prostatic Hyperplasia (BPH) In The Canine: Analysis Using Pennes Bioheat Equation" by Xu et al., *Advances In Bioheat And Mass Transfer*, vol. 268, pp. 31–35, 1993.

"2–D Finite Difference Modeling Of Microwave Heating In The Prostate" by Yuan et al., *Advance In Heat And Mass Transfer In Biotechnology*, vol. 32, pp. 107–115, 1995.

"Analysis Of Tissue and Arterial Blood Temperatures in the Resting Human Forearm" by Pennes, *Journal of Applied Physiology*, vol. 1, No. 2, pp. 93–122, Aug. 1948.

* cited by examiner

Primary Examiner—John P. Lacyk
Assistant Examiner—Brian Szmal
(74) Attorney, Agent, or Firm—Kinney & Lange, P.A.

(57) ABSTRACT

A non-invasive method of determining a temperature distribution in a targeted tissue volume treated with thermal therapy involves determining a baseline perfusion characteristic of the targeted tissue volume. A temperature distribution is calculated in the targeted tissue volume based on the baseline perfusion characteristic of the tissue, a microwave power input and a coolant temperature input. A perfusion characteristic of the targeted tissue volume is iteratively adjusted based on the calculated temperature distribution, and the temperature distribution is iteratively recalculated based on the adjusted perfusion characteristic, the microwave power input and the coolant temperature input throughout the thermal therapy.

20 Claims, 6 Drawing Sheets

FIG. 1
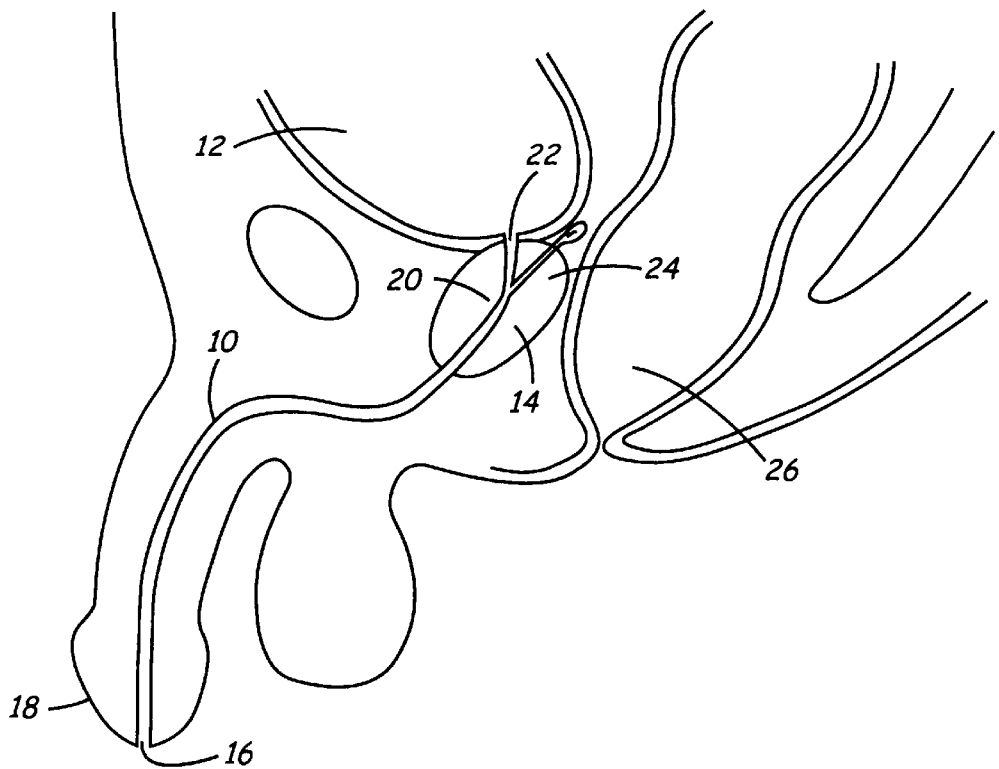
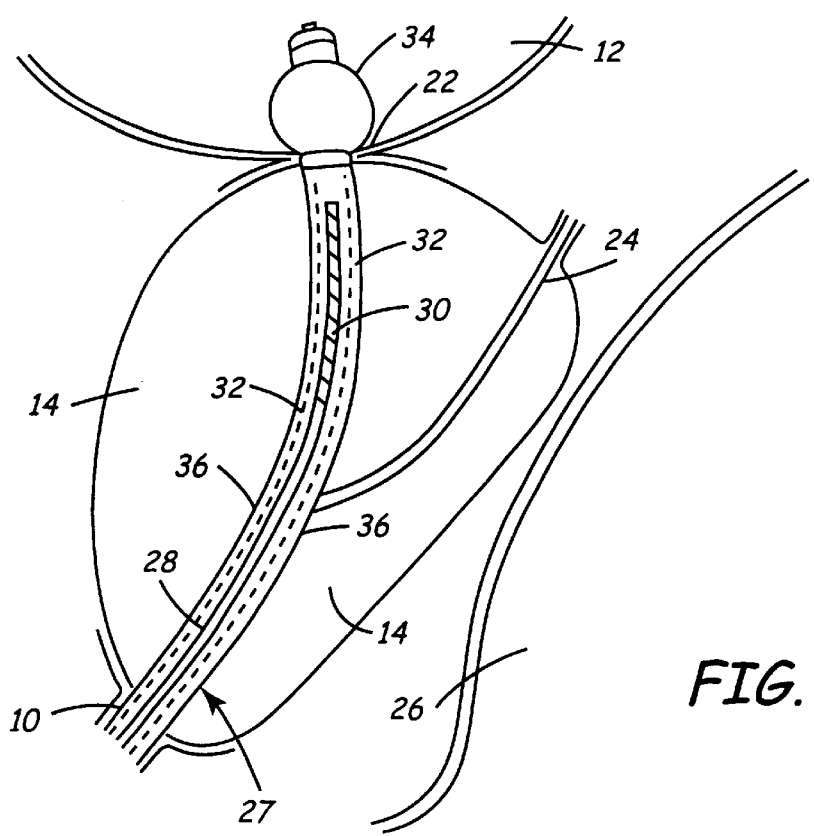
FIG. 2

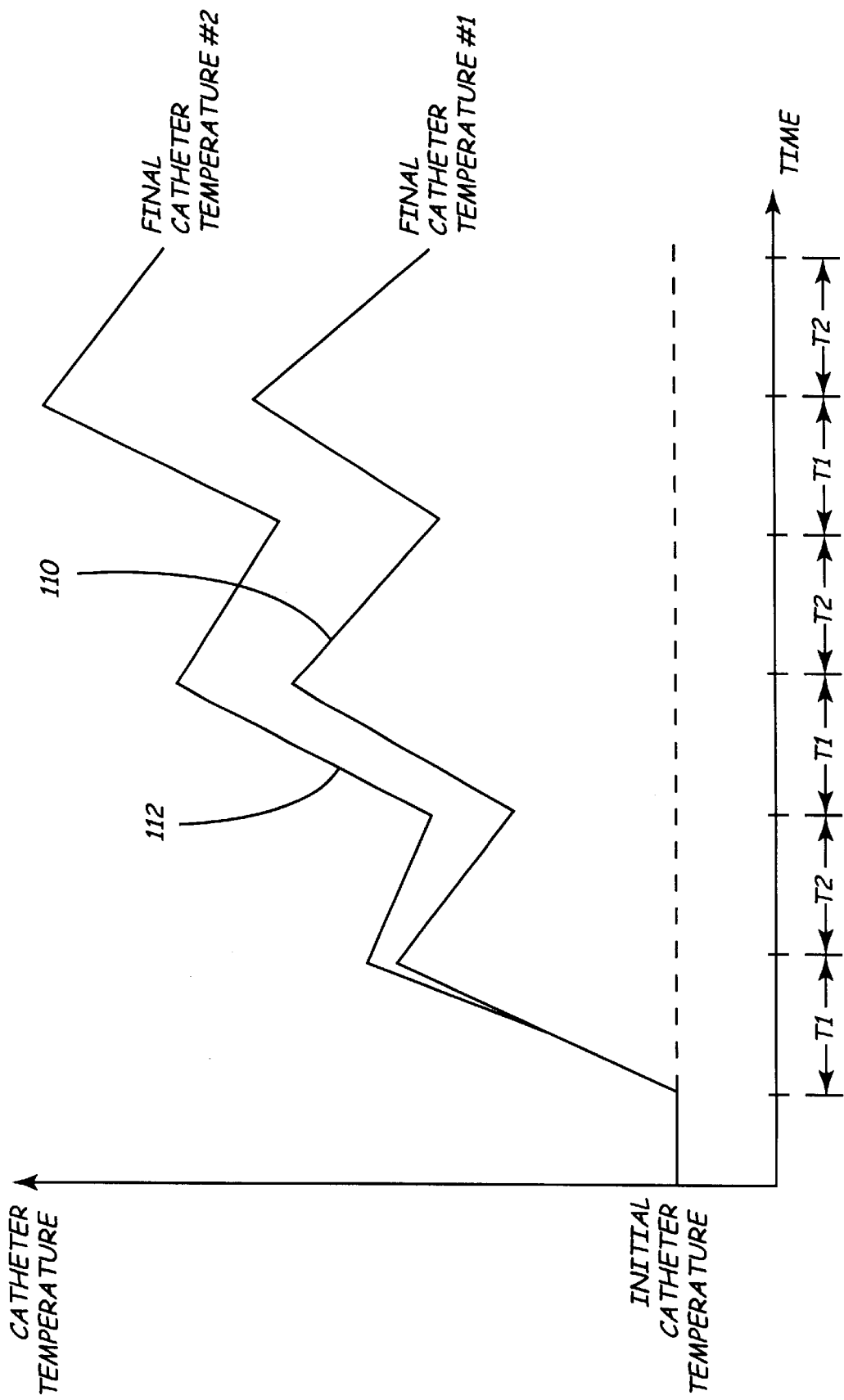

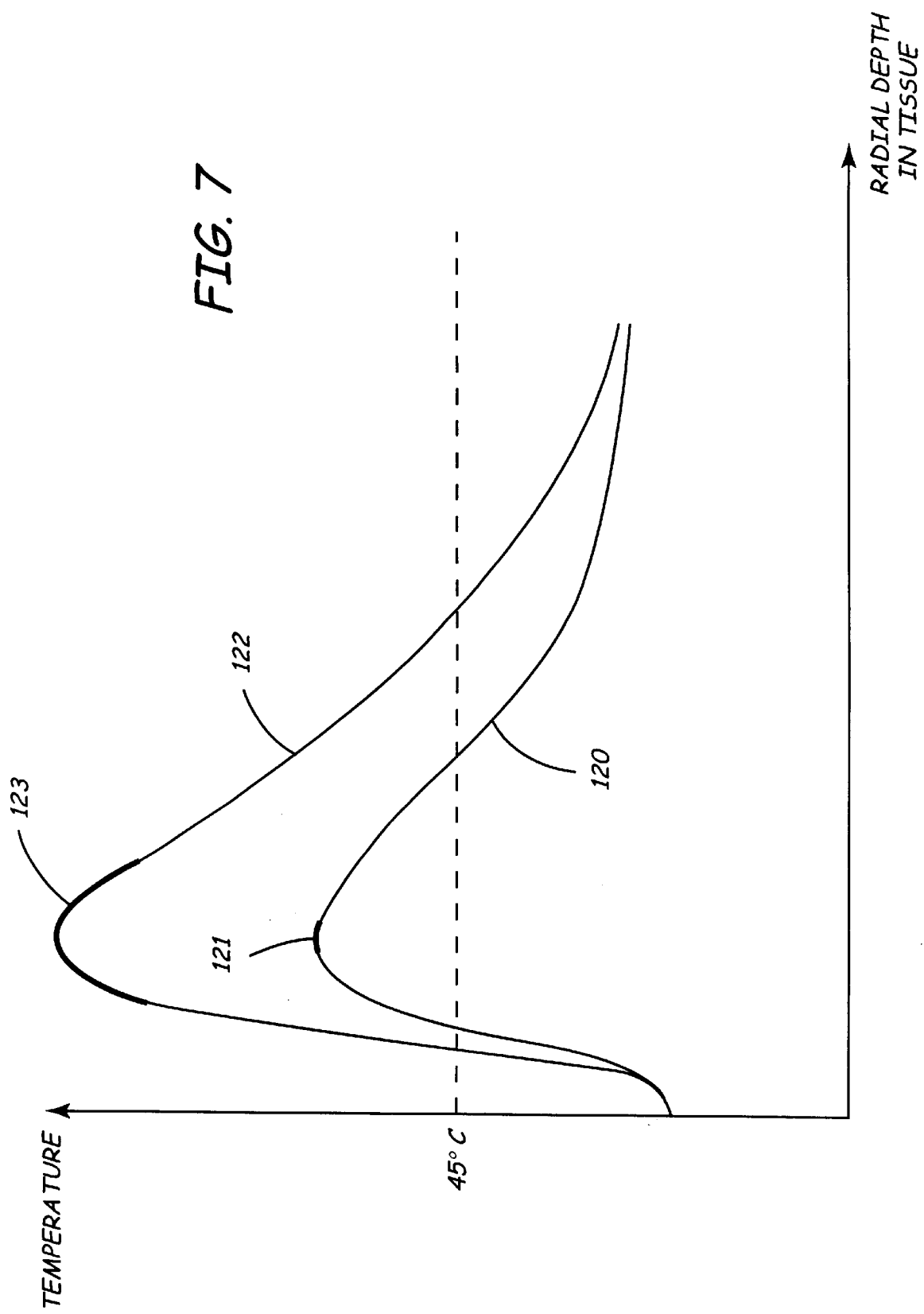

THERMODYNAMIC MODELING OF TISSUE TREATMENT PROCEDURE

BACKGROUND OF THE INVENTION

The present invention is a method of accurately and non-invasively predicting the temperature distribution in a volume of thermally treated tissue.

The prostate gland is a complex, chestnut-shaped organ which encircles the urethra immediately below the bladder. Nearly one third of the prostate tissue anterior to the urethra consists of fibromuscular tissue that is anatomically and functionally related to the urethra and the bladder. The remaining two thirds of the prostate is generally posterior to the urethra and is comprised of glandular tissue. The portion of the urethra extending through the prostate (i.e., the prostatic urethra) includes a proximal segment, which communicates with the bladder, and a distal segment, which extends at an angle relative to the proximal segment by the verumontanum.

Although a relatively small organ, the prostate is the most frequently diseased of all internal organs and is often the site of a common affliction among older men, benign prostatic hyperplasia (BPH), as well as a more serious affliction, cancer. BPH is a nonmalignant, bilateral expansion of prostate tissue occurring mainly in the transition zone of the prostate adjacent to the proximal segment of the prostatic urethra. As this tissue grows in volume, it encroaches on the urethra extending into the region of the bladder neck at the base of the bladder. Left untreated, BPH causes obstruction of the urethra which usually results in increased urinary frequency, urgency, incontinence, nocturia and slow or interrupted urinary stream. BPH may also result in more severe complications, such as urinary tract infection, acute urinary retention, hydronephrosis and uraemia.

Benign prostatic hyperplasia (BPH) may be treated using transurethral thermal therapy as described in U.S. Pat. No. 5,620,480 entitled METHOD FOR TREATING BENIGN PROSTATIC HYPERPLASIA WITH THERMAL THERAPY and in U.S. Pat. No. 5,575,811 entitled BENIGN PROSTATIC HYPERPLASIA TREATMENT CATHETER WITH URETHRAL COOLING, both of which are hereby incorporated by reference. During transurethral thermal therapy, the transition zone of the prostate is heated to necrose the tumorous tissue that encroaches on the urethra. Transurethral thermal therapy is administered by use of a microwave antenna-containing catheter which includes a multi-lumen shaft. The catheter is positioned in the urethra with the microwave antenna located adjacent to the hyperplastic prostatic tissue. Energization of the microwave antenna causes the antenna to emit electromagnetic energy which heats tissue within the prostate. A cooling fluid is circulated through the catheter to preserve tissue such as the urethral wall between the microwave antenna and the target tissue of the prostate. A rectal probe carrying a temperature sensor is often utilized as well, to ensure that the rectum is not overheated by the thermal therapy procedure.

In the process of performing thermal therapy of tissue as described in the above-referenced patents, it is desirable to ascertain the temperatures achieved in the tissue volume. Destruction of cells, or necrosis, in the targeted tissue volume is an objective of the thermal therapy. By monitoring the tissue temperature, necrosis may be determined according to the time/temperature relationship governing the response of the cells to heat levels above about 45° C. As a result, once a predetermined volume of necrosis has been achieved to relieve the patient from the symptoms of BPH, the thermal therapy session may be discontinued, thereby minimizing the overall therapy time. This is an important objective in a thermal therapy treatment, so that the patient receives an optimal dosage of thermal treatment and experiences a minimal level of discomfort and intimidation prior to and during the procedure, and also to allow a greater number of procedures to be performed in a fixed amount of time.

There are several practical obstacles to accurately measuring or modeling the temperatures achieved in the targeted tissue volume being treated. Interstitially introducing temperature sensors into the targetted tissue volume is a highly invasive procedure that requires piercing of the tissue, and tends to negate the advantages of delivering microwave energy from an adjacent body lumen or cavity. However, efforts to deduce the temperatures achieved in the targeted tissue volume are typically subject to a rather considerable error oruncertainty, since there are a number of parameters that vary rather significantly from patient to patient and therefore tend to inhibit accurate tissue temperature prediction. For example, the blood flow rate, or perfusion, in the tissue volume being treated varies among patients, and even changes throughout the procedure as cells in the tissue volume are heated and necrosed. The size of the tissue volume may also vary among patients, causing difficulties if a certain percentage of necrosis in the tissue volume is desired. Therefore, there is a continuing need in the art for an improved system for accurately and non-invasively predicting the temperature distribution achieved in a volume of thermally treated tissue.

BRIEF SUMMARY OF THE INVENTION

The present invention is a method of determining a temperature distribution in a targeted tissue volume treated with thermal therapy. A baseline perfusion characteristic of the targeted tissue volume is determined before commencement of thermal therapy. A temperature distribution is calculated and updated at periodic time interval in the targeted tissue volume based on the baseline perfusion characteristic, the currently prevailing microwave power input and the currently prevailing coolant temperature input. A perfusion characteristic of the targeted tissue volume is adjusted based on the calculated temperature distribution, and the temperature distribution is recalculated at the succeeding time interval based on the adjusted perfusion characteristic of the targeted tissue volume, the microwave power input and the coolant temperature input throughout the thermal therapy.

According to one aspect of the invention, calculations are performed for a plurality of sub-volumes in the targeted tissue volume. Determining the baseline perfusion characteristic of the targeted tissue volume involves ascertaining a baseline perfusion value for each sub-volume of tissue. The specification of a baseline perfusion value for each sub-volume of tissue may be performed by specifying baseline perfusion values for different zones of the targeted tissue volume. In addition, adjusting the perfusion characteristic of the targeted tissue volume may include adjusting a perfusion value for each sub-volume of tissue in the targeted tissue volume based on a temperature and location of the sub-volume of tissue.

According to a further aspect of the invention, a damage integral may be calculated throughout the thermal therapy to represent a percentage of cells necrosed in the targeted tissue volume. The damage integral is based on the time and temperature relationship for necrosis of the targeted tissue volume. The perfusion characteristic of the tissue may then be adjusted based on the calculated temperature and the calculated damage integral in the targeted tissue volume.

BRIEF DESCRIPTION OF THE DRAWINGS

FIG. 1 is a vertical section view of a male pelvic region showing the urinary organs affected by benign prostatic hyperplasia.

FIG. 2 is an enlarged view of the male pelvic region of FIG. 1 showing a urethral catheter positioned in the prostatic region.

FIG. 6 is a graphical diagram of the results of an exemplary baseline perfusion determination performed according to the method shown in FIG. 5.

FIG. 7 is a diagram illustrating a graphical temperature distribution and volume of necrosis display that can be produced according to the present invention.

DETAILED DESCRIPTION

Figure 3:
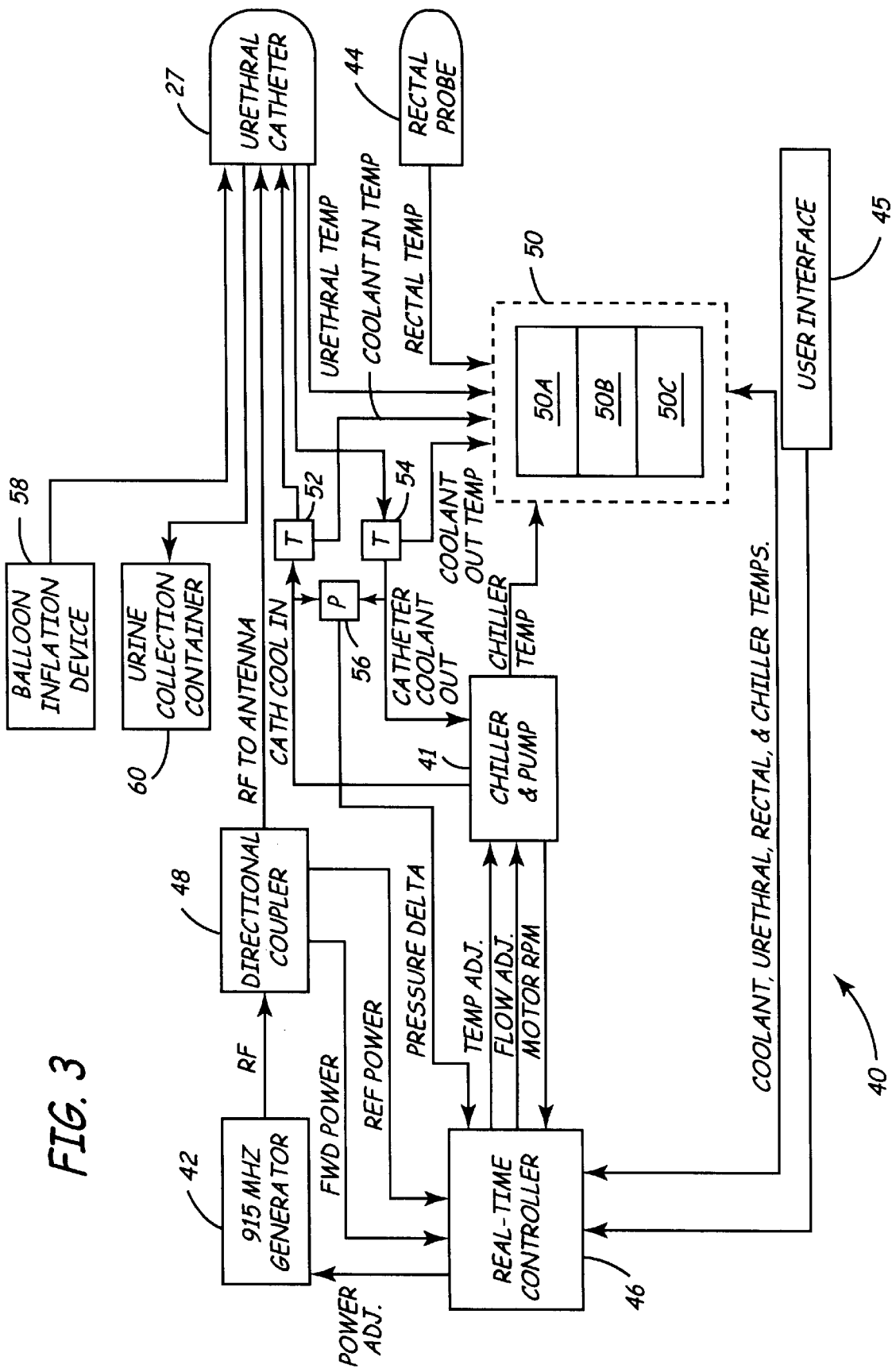
FIG. 3 is a block diagram of a thermal therapy treatment system for use with the present invention.

FIG. 1 is a vertical sectional view of a male pelvic region showing the effect benign prostatic hyperplasia (BPH) has on the urinary organs. Urethra 10 is a duct leading from bladder 12, through prostate 14 and out orifice 16 of penis end 18. Benign tumorous tissue growth within prostate 14 around urethra 10 causes constriction 20 of urethra 10, which interrupts the flow of urine from neck 22 of bladder 12 to orifice 16. The tumorous tissue of prostate 14 which encroaches urethra 10 and causes constriction 20 can be effectively removed by heating and necrosing the encroaching tumorous tissue. Ideally, periurethral tumorous tissue of prostate 14 anterior and lateral to urethra 10 is heated and necrosed to avoid unnecessary and undesirous damage to urethra 10 and to adjacent healthy tissues, such as ejaculatory duct 24 and rectum 26. A selective heating of benign tumorous tissue of prostate 14 (transurethral thermal therapy) may be achieved by utilizing a microwave antenna-containing catheter such as is shown in U.S. Pat. No. 5,620,480 or U.S. Pat. No. 5,575,811, which have been incorporated herein by reference.

FIG. 2 shows an enlarged view of the male pelvic region of FIG. 1 with a catheter 27 simplistically shown properly positioned within urethra 10. While the particular structure of catheter 27 may vary and a number of lumens may be provided therein, catheter 27 typically includes transmission line 28 connected to microwave antenna 30 for emitting microwave energy to prostate 14. Cooling fluid is circulated along paths 32 between microwave antenna 30 and the walls 36 of urethra 10, so as to conductively cool the tissue of urethra 10 when microwave antenna 30 is energized to radiate microwave energy to prostate 14. Catheter 27 may be secured within urethra 10 by retention balloon 34 located in bladder 12, for example. The temperature of the urethra may be detected by providing a temperature sensor on catheter 27 contacting urethral walls 36. In addition, the temperature of rectum 26 may be detected by inflating a balloon or providing another type of device in rectum 26 that includes a temperature sensor in contact with the rectal wall, such as is disclosed in U.S. Pat. No. 5,792,070 entitled RECTAL THERMOSENSING UNIT, which is hereby incorporated by reference.

FIG. 3 is a block diagram of thermal therapy treatment system 40 for use with the present invention, utilizing urethral catheter 27. System 40 includes cooling system 41, microwave generating source 42, user interface 45, real-time controller (RTC) 46, directional coupler 48, thermometry sensors 52 and 54, coolant pressure sensor 56, balloon inflation device 58 and urine collection container 60.

As shown in FIG. 3, control of microwave generating source 42 and cooling system 41 is effected by RTC 46, which is in turn controlled by user interface 45. User interface 45 is a computer system containing memory storage capability for data storage for backup purposes and for normal operation of system 40. User interface 45 communicates with RTC 46, which is responsible for all closed loop feedback to run system 40. RTC 46 has direct closed loop control of microwave power delivered by microwave generating source 42, and of coolant flow and coolant temperature of cooling system 41. Closed loop feedback tracks out variations in gain, drift and cable losses inherent in microwave generating source 42, and variability in pump output and refrigeration system efficiency of cooling system 41. In addition to monitoring microwave generating source 42 and cooling system 41, RTC 46 also monitors and controls several channels of thermometry via inputs from thermometry unit 50. Cooling system thermometry 50A measures the coolant and chiller temperatures based on signals from coolant temperature sensors 52 and 54 and a chiller temperature sensor (not shown) of cooling system 41. Urethral thermometry SOB measures urethral temperatures based on signals from a temperature sensor within catheter 27. Rectal thermometry 50C measures rectal temperature based upon signals received from a sensor (not shown) within rectal probe 44.

RTC 46 transmits all closed-loop feedback to user interface 45, which processes the input and transmits corrections and instructions back to RTC 46. RTC 46 interprets the instructions given to it by process control language received from user interface 45 and executes the instructions in real time. The instructions from user interface 45 are made to achieve proper therapy parameters when manual intervention is desired throughout the thermal therapy session. RTC 46may also automatically control therapy in the manner disclosed in pending U.S. application Ser. No. 09/210,033 entitled METHOD OF CONTROLLING THERMAL THERAPY, filed Dec. 11, 1998 by E. Rudie, J. Flachman, J. Burgett and T. Larson, which is hereby incorporated by reference. In addition, system 40 includes a hardware fail-safe circuit which shuts down system 40 should any parameter fall outside a given range of values. The thermal model disclosed herein may be implemented to assist with therapy control in a system employing manual or automatic control of the therapy, or a combination of both.

The thermal model is based on the thermodynamic energy balance embodied in the Pennes bioheat equation. The Pennes bioheat equation is a differential equation obtained by establishing energy balances for each infinitesimal sub-volume of the thermally treated tissue. Each sub-volume is a tiny, imaginary volume of tissue through which heat can be transported by conduction. In addition, there can be blood flow through each sub-volume that connects heat into and out of the tissue. Microwave energy absorbed in the sub-volume of tissue provides a further source of heat. Solving the differential Pennes bioheat equation with appropriate boundary conditions yields the temperature distribution throughout the entire tissue volume, i.e., throughout the prostate.

The Pennes equation may be expressed symbolically by the following energy balance:

$$E(\text{inflow}) - E(\text{outflow}) + E(\text{generation}) = E(\text{stored}) \quad (1)$$

where E(inflow) is the rate of heat inflow to the sub-volume by heat conduction and blood flow, E(outflow) is the rate of heat outflow from the sub-volume by heat conduction and blood flow, E(generation) is the rate of heat generation in the sub-volume by microwave absorption, and E(stored) is the rate of heat storage in the tissue by temperature elevation. Each of these 'E' terms is expressed by appropriate mathematical expressions to yield the Pennes bioheat equation. Embedded within these mathematical expressions are various properties of the tissue including density, specific heat, thermal conductivity and rate of blood perfusion. The E(generation) term is given by the known microwave deposition pattern provided by the antenna utilized in the treatment catheter, and is dependent on the antenna geometry, catheter geometry, power input to the antenna, and the basic dielectric properties of the tissue.

In order to predict the temperature distribution within the targeted tissue volume, the Pennes bioheat equation must be solved subject to appropriate boundary conditions. At the surface of the catheter (which is the inner boundary of the calculation region), the boundary condition is specified by the measured temperature of the coolant and the known "heat transfer coefficient" between the tissue and the coolant. At the outer boundary of the calculation region, which is taken to be so far from the catheter that the temperature elevation there is negligible, the conduction heat flow rate is assumed to be zero.

The solution to the bioheat equation is obtained by a finite-difference method. The calculation region is divided into finite-sized sub-volumes of tissue that are taken to be sufficiently small so as to convert the differential expressions in the energy balance to algebraic expressions with an excellent degree of approximation. An algebraic equation is thus obtained for each sub-volume of tissue. Simultaneous solution of these algebraic equations by standard linear algebra techniques yields the temperature at the center of each tissue sub-volume, which provides an excellent approximation of the true, continuous temperature distribution in the tissue.

The time-wise variations of temperatures in the targeted tissue volume are tracked by subdividing time into short, discrete intervals or time steps, such as one second intervals in an exemplary embodiment. The solution process is started from the known initial conditions of the targeted tissue. A single time interval is allowed to elapse, and the solution to the bioheat equation is recomputed at the end of the time step. This new solution forms the starting condition for the next time step, and an updated temperature field is then calculated following the expiration of another time interval. The process is repeated, with each newly computed temperature field forming the initial condition for the next time step. To simulate the entire therapy, the appropriate number of time steps are taken to encompass the entire duration of the therapy. During the course of therapy, real-time inputs for coolant temperature and the power input to the antenna are required to enable the real-time prediction of the temperature field in the targeted tissue throughout the course of the therapy.

Figure 4:
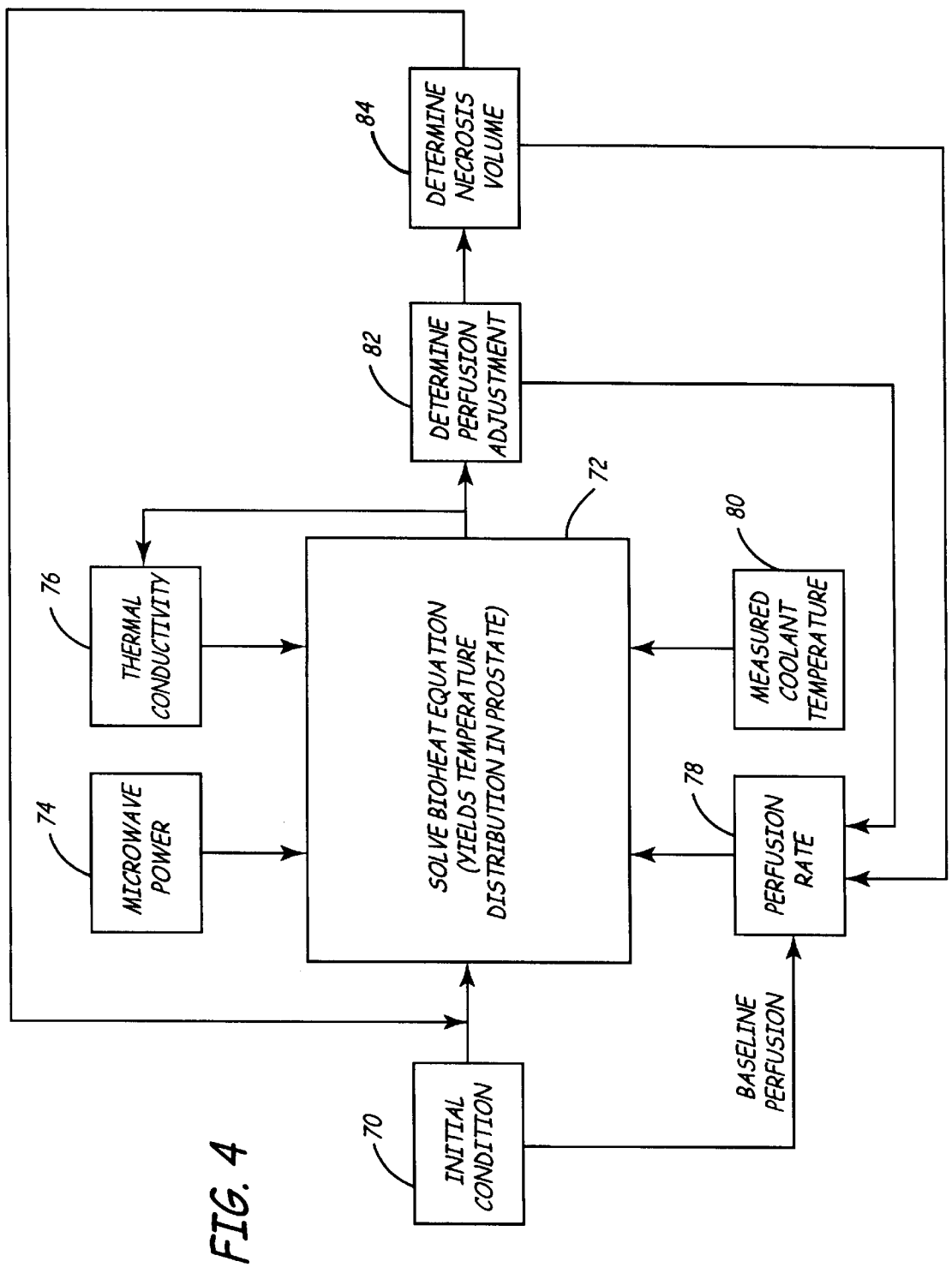
FIG. 4 is a block diagram of the thermodynamic modeling method of the present invention.

FIG. 4 is a block diagram of the thermodynamic modeling method of the present invention. An initial condition of the targeted tissue volume (i.e. a prostate) is determined in the first instance at functional block 70. This initial condition includes an initial temperature of the tissue and a baseline perfusion rate in the tissue. The initial tissue temperature is input to mathematical modeling block 72, along with a microwave power input (block 74), a tissue thermal conductivity input (block 76), a perfusion rate input (block 78) and a measured coolant temperature input (block 80). Based on this set of input parameters, the bioheat equation may be solved in modeling block 72 to yield a temperature distribution in the prostate. The temperature of tissue in the prostate is utilized to adjust the thermal conductivity input (block 76), since thermal conductivity is highly dependent on temperature. The relationship of the thermal conductivity of tissue and temperature is based on in-vitro experimental measurements that are known in the art.

The rate of blood perfusion in tissue is also dependent on temperature, time of exposure to elevated temperatures, and the location of the tissue within the prostate. In turn, the rate of blood perfusion affects the temperature elevation of tissue in response to continued exposure to microwaves. Therefore, in order to accurately model the temperature distribution in the prostate, the rate of blood perfusion must be continually updated for each iterative solution of the bioheat equation. Therefore, a perfusion adjustment is determined at functional block 82, based on the temperature and location of the prostatic tissue, to adjust the perfusion rate input (block 78) to the mathematical model. Specifically, for a relatively simple one-dimensional thermal model, the prostate is conceptually divided into three zones: a peri-urethral region encompassing the inner 5 millimeters (mm) of the prostate radius, a middle region extending from the 5 mm radius to the prostatic capsule, and an outer region extending from the prostatic capsule to the outer edge of the calculation region. It should be understood that these regional boundaries in the prostate are exemplary for one preferred embodiment of the invention, and the boundaries are adjustable in order to modify the performance of the thermal model as desired. In addition, although not explicitly shown in the exemplary model depicted in FIG. 4, the size of the prostatic capsule may be an additional input to the model, determined by ultrasound or a similar method. At the inception of the thermal treatment, the peri-urethral baseline perfusion is taken to be 1.5 times higher than the middle region, and the outer region is assigned a baseline perfusion of 0.0012 milli-liters per second per milli-liter of tissue (ml/sec/ml). In order to simulate the change in perfusion due to thermoregulatory vaso-dilation that occurs in tissue during thermal treatment, a set of modeling rules are implemented as follows:

In peri-urethral zone
  If temperature exceeds 40° C., perfusion=1.50×baseline value
  If temperature exceeds 43° C., perfusion=2.50×baseline value
  If temperature exceeds 48° C., perfusion=3.50×baseline value
In middle and outer zones
  If temperature exceeds 40° C., perfusion=1.20×baseline value
  If temperature exceeds 43° C., perfusion=1.35×baseline value
  If temperature exceeds 48° C., perfusion=1.60×baseline value The modeling rules shown above are exemplary for one preferred embodiment of the invention. For example, in another embodiment of the invention, the modeling rules may be implemented as a continuous function of temperature, rather than a step-wise function of temperature, to vary the characteristics of the model. One skilled in the art will recognize that the thermal model may also be executed in two dimensions, with the higher perfusion in anterior prostate tissue (opposite the rectum) and the lower perfusion in posterior prostate tissue (adjacent the rectum) being taken into account. Similarly, the model may be executed in three dimensions, with the higher perfusion in tissue adjacent the bladder neck and the lower perfusion in tissue distant from the bladder neck being taken into account Each additional dimension of the model requires significant additional computing resources to accommodate the increase in the number of tissue sub-volumes being modeled.

In one embodiment, a measured temperature may also be utilized to check on the model's estimate of perfusion, to enable greater modeling accuracy. A point in the tissue having a known location and temperature is taken, and the measured temperature is compared with the temperature predicted by the model at that location. Based on the difference between the measured and predicted temperatures, the model can adjust either the perfusion baseline, the perfusion adjustment rules, or both, to more accurately reflect the true conditions of the prostate consistent with the measured temperature. In order to ensure that proper adjustments are made to the perfusion baseline and/or adjustment rules, the model must also recalculate the temperatures at previous times in the therapy to ensure that the predicted temperatures based on the new perfusion baseline or perfusion adjustment rules are consistent with the actual measured temperatures at the corresponding previous times.

In addition to the perfusion adjustment determined at block 82 to account for vaso-dilation effects, a necrosis volume is also determined at functional block 84 based on heating of prostate tissue for a length of time sufficient to thermally damage the tissue. More specifically, a "damage integral" representing the fraction of cells that have been destroyed in each sub-volume of the prostate is calculated throughout the treatment. Calculation of the damage integral requires knowledge of the chemical kinetic rate constant for the damage mechanism of cells in the prostate, which varies strongly with temperature. The rate constant and its variation with temperature are established by comparing the predictions of the thermal model against experimentally measured interstitial temperatures in a number of patients during a thermal therapy procedure. Specifically, the Arrhenius rate constant model establishes the chemical kinetic rate constant of tissue as:

$$k = k_0 \times 10^{\left(\frac{T-T_0}{Z}\right)} \quad (2)$$

where k is the rate constant, $k_0$ is the baseline rate constant at a fixed temperature such as about 45° C., T is the temperature, $T_0$ is the baseline temperature of about 45° C., and Z is a true constant. The true constant Z is determined by performing a thermal therapy procedure while interstitially measuring prostatic temperatures, thereby providing known values for all of the other variables in equation 2. The damage integral can then be calculated as follows:

$$\frac{N}{N_0} = \exp\left(-\int_0^\tau k\, dt\right) \quad (3)$$

where N is the number of remaining viable cells in the tissue sub-volume, $N_0$ is the initial number of viable cells in the tissue sub-volume, τ is the duration of the thermal therapy, and k is the rate constant of the tissue.

In order to simulate the dramatic decrease in perfusion due to thermoregulatory vaso-constriction that occurs in tissue after exposure to thermal treatment, a further set of modeling rules are implemented as follows:
In peri-urethral zone
Once 99.9% of the cells have been necrosed, the perfusion drops to residual level of 1.13×baseline value.
In middle and outer zones
Once 70% of the cells have been necrosed, the perfusion drops to residual level of 0.20×baseline value.

The modeling rules shown above are exemplary for one preferred embodiment of the present invention.

The perfusion rate input (block 78) to mathematical bioheat model 72 is thus also adjusted based on the level of necrosis determined at functional block 84, as shown in FIG. 4. The determination of a volume of necrosis (where necrosis is defined as a damage integral of a predetermined percentage) is also important to signify to a treating physician when therapy is complete and may be discontinued. By accurately modeling temperature and the extent of necrosis during a treatment session, the total session time can be minimized for each patient, which is highly desirable to optimize the thermal dosage received by the patient, to reduce discomfort and intimidation associated with the therapy and to reduce physician time required to perform the therapy.

Once the thermal conductivity (block 76) and perfusion rate (block 78) parameters have been updated, another iteration of the solution of the bioheat equation is performed in modeling block 72, taking the previously calculated temperature distribution as the initial condition for each tissue sub-volume. For each iteration, the measured microwave power input (block 74) and the measured coolant temperature input (block 80) are updated as well. The resulting temperature distribution model provides a highly accurate predictive representation of the effects of thermal therapy on the prostate.

Figure 5:
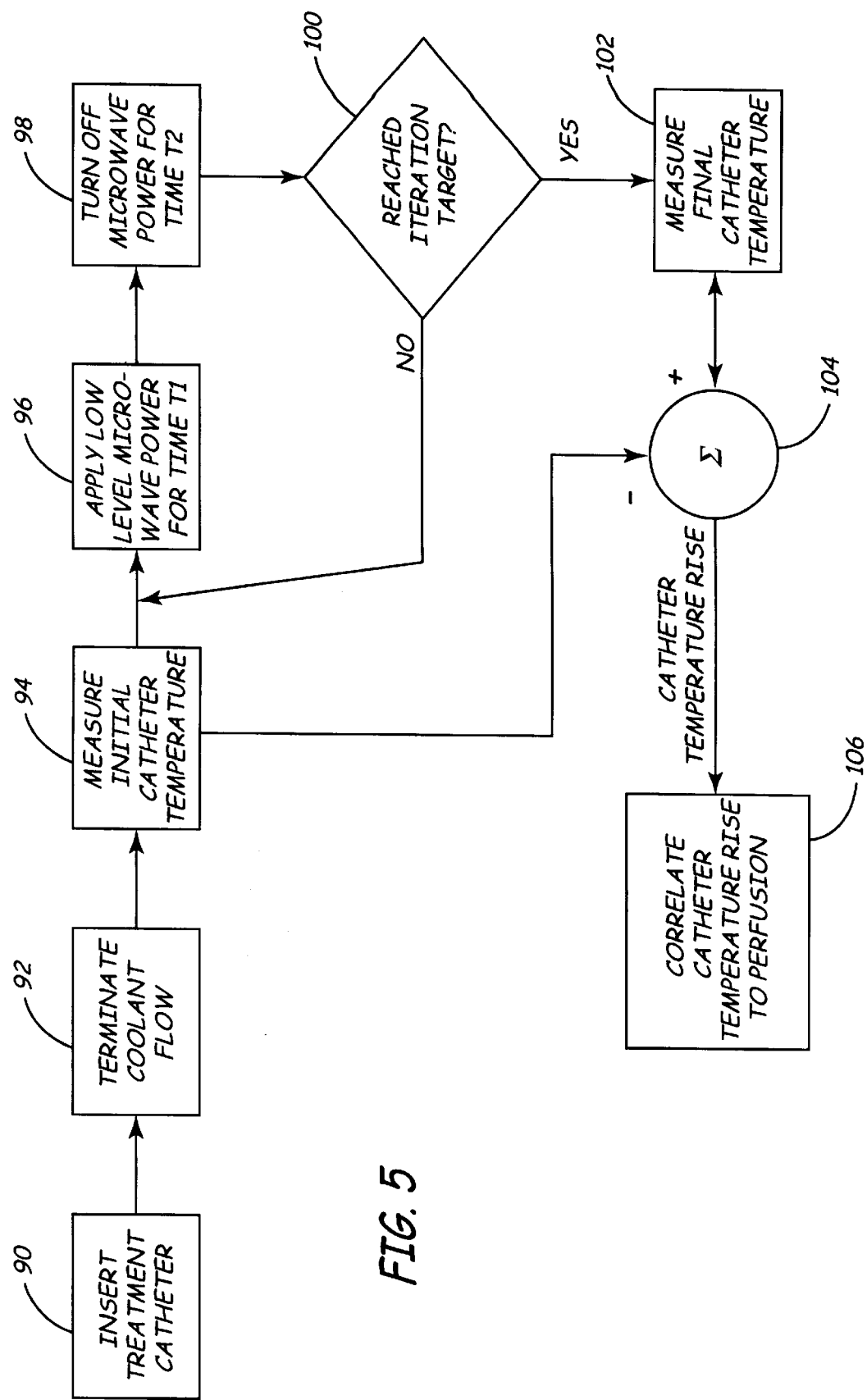
FIG. 5 is a flow diagram of a method of establishing an individualized baseline perfusion rate according to the present invention.

As shown in FIG. 4, determining the initial conditions of the prostate tissue, depicted by functional block 70, requires the establishment of a baseline blood perfusion rate. This baseline blood perfusion rate is unique for each individual patient, and therefore must be determined on a patient-by-patient basis. FIG. 5 is a flow diagram of a method of establishing an individualized baseline perfusion rate according to the present invention. The urethral treatment catheter is first inserted as indicated at block 90. The flow of coolant through the catheter is terminated at block 92. The initial catheter temperature is then measured at block 94, with the catheter temperature reading being based on the temperature of the coolant circulating through the catheter, if any (in this case there is no coolant flow) and the temperature of the tissue adjacent to the catheter. Thus, the measured catheter temperature is indicative of the temperature of the tissue adjacent to the catheter. Low-level microwave power, such as five watts of power in an exemplary embodiment, is then delivered from the catheter for a time period T1, as indicated at block 96, and microwave power is subsequently turned off for a time period T2, as indicated at block 98. In an exemplary embodiment, time T1 is 25 seconds and time T2 is 35 seconds. The steps performed at blocks 96 and 98 are repeated for a selected number of iterations, as symbolically illustrated by decision block 100. In an exemplary embodiment, the selected number of iterations is three. Once the iteration target has been reached, the final catheter temperature is measured at block 102. The difference between the final catheter temperature and the initial catheter temperature is the catheter temperature rise due to the application of microwave power, and the calculation of which is symbolically illustrated by the adding of the final catheter temperature and the subtracting of the initial catheter temperature at block 104. The catheter temperature rise is then correlated to a baseline rate of blood perfusion at block 106, according to empirically accumulated test data, to yield an individualized baseline perfusion rate for use in the thermodynamic modeling method of the present invention. The baseline rate of perfusion measured in this way is more strongly reflective of the perfusion in the peri-urethral zone than of the perfusion in the middle or outer zones However, since it is assumed that a fixed relationship exists between the perfusion rates in the peri-urethral and middle zones, the measured catheter temperature rise can be correlated to the baseline perfusion rates in both of those zones.

The results of exemplary baseline perfusion determinations are shown graphically in FIG. 6. Curve 110 shows the results of a baseline perfusion determination procedure with a relatively high perfusion rate, and curve 112 shows the results of a baseline perfusion determination procedure with a relatively low perfusion rate. The initial catheter temperature is measured, and then low-level microwave power is delivered for time period T1. As shown in FIG. 6, catheter temperature increases more quickly for the low perfusion case (curve 112) than the high perfusion case (curve 110). Next, microwave power is discontinued for time period T2. This process is repeated for three iterations, yielding final catheter temperature #1 for curve 110 and final catheter temperature #2 for curve 112 The difference between the final catheter temperature and the initial catheter temperature corresponds to a unique perfusion rate in the tissue, with a higher temperature difference corresponding to a lower rate of perfusion, as illustrated in FIG. 6.

As discussed above with respect to FIG. 4, a volume of necrosis can be determined from the temperature distribution model of the present invention, based on the time-temperature relationship of thermal damage to prostate tissue. In order to convey information pertaining to the volume of necrosis to a physician or technician performing the therapy, a graphic display such as is shown in FIG. 7 is beneficial. FIG. 7 shows a graphical display of temperature versus radial depth in tissue at a first point in time during therapy (curve 120) and at a second, later point in time during therapy (curve 122). The curves illustrate the temperature of tissue according to the thermodynamic model of the present invention, and the highlighted portions of the curves (portion 121 of curve 120, and portion 123 of curve 123) indicate the volume of tissue that has been necrosed, based on the time-temperature relationship of thermal damage to the tissue. This information provides a graphical indication of the progress of the therapy, and enables the therapy to be discontinued when a desired volume of necrosis has been achieved for each individual patient. In other alternate embodiments, the display may take other forms, such as a curve having colors along its spatial expanse that vary to represent the damage integral associated with various depths of tissue, or a pair of curves where one curve represents the temperature and the other curve represents the damage integral associated with the various depth of tissue. Other modifications of the display to convey information relating to the temperatures and thermal damage in the tissue are also contemplated by the present invention.

The present invention provides an accurate predictive thermodynamic model of a temperature distribution in targeted tissue during thermal therapy. Both interstitial temperatures and a zone of necrosis are predicted non-invasively by the model, taking into account the changing perfusion characteristics of the tissue as therapy progresses. The model is also individualized for each patient, making a baseline perfusion determination on a patient-by-patient basis to be input into the model. Prostate size may also be input into the model. As a result, highly accurate temperature distribution readings are available to monitor and control the therapy, providing the potential for improved efficiency and reduced therapy time as therapy is performed on each patient.

Although the present invention has been described in the context of a particular treatment modality, namely delivery of microwaves to the targeted tissue with a coolant circulated between the microwave antenna and the tissue, the thermal model may be utilized with other forms of thermal therapy as well. The other forms of thermal therapy merely dictate different boundary conditions in the thermal model, as well as a different system for determining a baseline perfusion characteristic of the tissue. Thus, the present invention provides a thermal modeling method for determining a temperature distribution in a tissue region treated by thermal therapy that is individualized, accurate, versatile and non-invasive.

Although the present invention has been described with reference to preferred embodiments, including exemplary values of parameters utilized to practice the invention, workers skilled in the art will recognize that changes may be made in form and detail, including variation of the parameter values, without departing from the spirit and scope of the invention.

What is claimed is:

1. A method of determining a temperature distribution in a targeted tissue volume treated with thermal therapy, the method comprising:

determining a baseline perfusion characteristic of the targeted tissue volume before commencement of thermal therapy;

calculating a temperature distribution in the targeted tissue volume based on the baseline perfusion characteristic, a microwave power input and a coolant temperature input upon commencement of the thermal therapy; and iteratively adjusting a perfusion characteristic of the targeted tissue volume based on the calculated temperature distribution and recalculating the temperature distribution based on the adjusted perfusion characteristic, the microwave power input and the coolant temperature input throughout the thermal therapy.

2. The method of claim 1, further comprising:

determining a volume of necrosis in the targeted tissue volume based on the time and temperature relationship therein.

3. The method of claim 2, further comprising adjusting the perfusion characteristic of the targeted tissue volume based on the determined volume of necrosis.

4. The method of claim 3, further comprising graphically displaying the calculated temperatures and the determined volume of necrosis within the targeted tissue volume.

5. The method of claim 2, wherein determining a volume of necrosis comprises calculating a damage integral throughout the thermal therapy representative of a percentage of cells necrosed in the targeted tissue volume, the damage integral being based on the time and temperature relationship in the targeted tissue volume, and further comprising adjusting the perfusion characteristic of the targeted tissue volume based on the calculated damage integral.

6. The method of claim 1, wherein determining a baseline perfusion characteristic of the targeted tissue volume comprises:

inserting a treatment catheter in a urethra adjacent the targeted tissue volume;

terminating coolant flow through the treatment catheter;

measuring an initial catheter temperature;

applying microwave power from the catheter for a first time period;

discontinuing microwave power from the catheter for a second time period;

repeating the steps of applying and discontinuing microwave power for a selected number of iterations;

measuring a final catheter temperature; and comparing the initial catheter temperature to the final catheter temperature to determine a corresponding baseline perfusion value.

7. The method of claim 1, further comprising:

measuring a temperature of a point in the targeted tissue volume;

comparing the measured temperature of the point in the targeted tissue volume to a predicted temperature of the point in the targeted tissue volume from the calculated temperature distribution in the targeted tissue volume; and adjusting the perfusion characteristic of the targeted tissue volume based on a difference between the measured temperature and the predicted temperature of the point in the targeted tissue volume.

8. A method of determining a temperature distribution in a targeted tissue volume comprising a plurality of sub-volumes treated with thermal therapy, the method comprising:

(a) determining an initial condition of each sub-volume of tissue in the targeted tissue volume;

(b) calculating a temperature for each sub-volume of tissue in the targeted tissue volume based on the initial condition of each sub-volume of tissue in the targeted tissue volume, a microwave power input and a coolant temperature input;

(c) adjusting the targeted tissue volume condition based on the calculated temperature for each sub-volume of tissue in the targeted tissue volume to yield an adjusted condition;

(d) calculating the temperature for each sub-volume of tissue in the targeted tissue volume based on the adjusted condition of the targeted tissue volume, the microwave power input and the coolant temperature input; and (e) repeating steps (c) and (d) throughout the thermal therapy.

9. The method of claim 8, wherein determining an initial condition of the targeted tissue volume comprises ascertaining a baseline perfusion value for each sub-volume of tissue in the targeted tissue volume.

10. The method of claim 9, wherein a baseline perfusion value for each sub-volume of tissue in the targeted tissue volume is ascertained by:

determining a first baseline perfusion value for a peri-urethral zone of the targeted tissue;

establishing a second baseline perfusion value for a middle zone of the targeted tissue between the peri-urethral zone of the targeted tissue and an outer boundary of a prostatic capsule, the second baseline perfusion value being related to the first baseline perfusion value; and establishing a third baseline perfusion value for an outer zone of the targeted tissue outside of the prostatic capsule.

11. The method of claim 10, wherein determining the first baseline perfusion value for the peri-urethral zone of the targeted tissue comprises:

(i) inserting a treatment catheter in a urethra adjacent the targeted tissue volume;

(ii) terminating coolant flow through the treatment catheter;

(iii) measuring an initial catheter temperature;

(iv) applying microwave power from the catheter for a first time period;

(v) discontinuing microwave power from the catheter for a second time period;

(vi) repeating steps (iv) and (v) for a selected number of iterations;

(vii) measuring a final catheter temperature; and (viii) comparing the initial catheter temperature to the final catheter temperature to determine a corresponding baseline perfusion value.

12. The method of claim 9, wherein adjusting the targeted tissue volume condition comprises adjusting a perfusion value for each sub-volume of tissue in the targeted tissue volume based on a temperature and location of the sub-volume of tissue.

13. The method of claim 12, wherein adjusting the perfusion value for each sub-volume of tissue in the targeted tissue volume based on the temperature and location of the sub-volume of tissue comprises setting the perfusion value to a predetermined multiple of the baseline perfusion value for each sub-volume of tissue in the targeted tissue volume, the predetermined multiple being based on the temperature and location of the sub-volume of tissue.

14. The method of claim 8, further comprising:

(f) calculating a damage integral throughout the thermal therapy representative of a percentage of cells necrosed in each sub-volume of tissue in the targeted tissue volume, the damage integral being based on the time and temperature relationship of each sub-volume of tissue in the targeted tissue volume; and (g) adjusting the targeted tissue volume condition based on the location, the calculated temperature and the calculated damage integral for each sub-volume of tissue in the targeted tissue volume to yield the adjusted condition.

15. The method of claim 14, further comprising:

(h) graphically displaying the calculated temperatures and a volume of necrosis within the targeted tissue volume.

16. The method of claim 7, further comprising:

measuring a temperature of a point in the targeted tissue volume;

comparing the measured temperature of the point in the targeted tissue volume to a calculated temperature of the sub-volume of tissue in the targeted tissue volume that includes the point whose temperature is measured; and adjusting the targeted tissue volume condition based on a difference between the measured temperature of the point in the targeted tissue volume and the calculated temperature of the sub-volume of tissue in the targeted tissue volume that includes the point whose temperature is measured.

17. A method of determining a temperature distribution in a targeted tissue volume treated with thermal therapy, the method comprising:

calculating a temperature distribution in the targeted tissue volume based on a microwave power input and a coolant temperature input upon commencement of the thermal therapy;

iteratively adjusting a perfusion characteristic of the targeted tissue volume based on the calculated temperature distribution; and recalculating the temperature distribution based on the adjusted perfusion characteristic, the microwave power input and the coolant temperature input throughout the thermal therapy.

18. The method of claim 17, further comprising:

determining a volume of necrosis in the targeted tissue volume based on the time and temperature relationship therein.

19. The method of claim 18, further comprising adjusting the perfusion characteristic of the targeted tissue volume based on the determined volume of necrosis.

20. The method of claim 17, further comprising:

measuring a temperature of a point in the targeted tissue volume;

comparing the measured temperature of the point in the targeted tissue volume to a predicted temperature of the point in the targeted tissue volume from the calculated temperature distribution in the targeted tissue volume; and adjusting the perfusion characteristic of the targeted tissue volume based on a difference between the measured temperature and the predicted temperature of the point in the targeted tissue volume.

* * * * *